United States Patent
Toubia et al.

(10) Patent No.: US 7,803,154 B2
(45) Date of Patent: *Sep. 28, 2010

(54) CRYOGENIC PROBE FOR TREATING ENLARGED VOLUME OF TISSUE

(75) Inventors: Didier Toubia, Raanana (IL); Alexander Levin, Binyamina (IL); Miron Kaganovich, Haifa (IL)

(73) Assignee: Arbel Medical Ltd., Caesarea (IL)

( * ) Notice: Subject to any disclaimer, the term of this patent is extended or adjusted under 35 U.S.C. 154(b) by 259 days.

This patent is subject to a terminal disclaimer.

(21) Appl. No.: 11/832,778

(22) Filed: Aug. 2, 2007

(65) Prior Publication Data

US 2008/0033416 A1 Feb. 7, 2008

Related U.S. Application Data

(63) Continuation-in-part of application No. 11/462,244, filed on Aug. 3, 2006, now Pat. No. 7,425,211.

(51) Int. Cl.
*A61B 18/02* (2006.01)
(52) U.S. Cl. .......................................... 606/20; 606/23
(58) Field of Classification Search ............. 606/20–28; 607/88, 89; 128/898
See application file for complete search history.

(56) References Cited

U.S. PATENT DOCUMENTS

| | | | |
|---|---|---|---|
| 5,885,276 A * | 3/1999 | Ammar et al. ................ 606/21 |
| 6,565,556 B1 * | 5/2003 | Korpan et al. ................ 606/23 |
| 6,913,604 B2 | 7/2005 | Mihalik | |
| 6,942,659 B2 | 9/2005 | Lehmann | |
| 6,951,569 B2 | 10/2005 | Nohilly | |
| 6,954,977 B2 | 10/2005 | Maguire | |
| 6,995,493 B2 | 2/2006 | Isoda | |
| 7,001,378 B2 | 2/2006 | Yon | |
| 7,025,767 B2 | 4/2006 | Schaefer | |
| 7,425,211 B2 * | 9/2008 | Levin et al. ................... 606/20 |
| 2005/0177147 A1 * | 8/2005 | Vancelette et al. ........... 606/21 |
| 2006/0293647 A1 * | 12/2006 | McRae et al. ................ 606/27 |
| 2008/0114346 A1 * | 5/2008 | Levin et al. ................... 606/23 |

* cited by examiner

*Primary Examiner*—Ahmed M Farah
(74) *Attorney, Agent, or Firm*—Heslin Rothenberg Farley & Mesiti P.C.

(57) ABSTRACT

A cryoprobe for surgical and other treatments. The cryoprobe comprises an expandable section that performs displacement of a distal cryotip forwards when there is elevation of the operation pressure in the interior of the cryoprobe. Needle-wise metal elements are installed on the external side of the cryotip. These needle-wise elements are deflecting outwards by a deflecting member fastened on the distal edge of an external shaft of the cryoprobe. This allows a significant enlargement of the frozen volume of the treated tissue with the same operation temperature and the outer diameter of the cryoprobe. In another embodiment, the needle elements are formed in a displaceable metal sheath and a distal section of a cryotip and/or special protrusions on this distal section act as the deflecting member.

18 Claims, 12 Drawing Sheets

CRYOGENIC PROBE FOR TREATING ENLARGED VOLUME OF TISSUE

FIELD OF THE INVENTION

The present invention is directed to providing a cryogenic probe for medical applications, such as surgery.

BACKGROUND OF THE INVENTION

Cryogenic technology provides cooling to very low temperatures. It is widely used in medicine, and particularly in surgery. Freezing tissue can kill its cells, and this makes cryosurgery particularly useful for treating cancerous growths. A cryogenic-probe may be used to kill the cells of malignant cysts in mammary tissue. The cryoprobe is required to have a small diameter to cause minimal damage and trauma to the body tissue in its passage through body tissue.

Typically, the site requiring treatment is significantly larger than the diameter of the cryoprobe and is all too frequently wider than the effectively frozen volume of tissue that is treatable by a single probe insertion. Use of multiple probes causes additional trauma and discomfort. Indeed, it will be appreciated that resorting to such procedures will invariably cause trauma to a large volume of tissue contacted along the entire length of the cryogenic probe used to bring the probe tip to its destination.

One interesting development that addresses the issue of treating a considerably larger volume of tissue than that in proximity to the shaft of the ablation needle is described in Schaefer (U.S. Pat. No. 7,025,767), which relates to a tumor ablation needle for use to treat ablated tumors with RF energy. The tumor ablation needle described therein comprises a needle with a spreading array of individually traversing conductive tines that are independently positioned. Specifically, the disclosure describes an ablation probe comprising: an elongated member having an exterior wall, a proximal end, and a distal end; a plurality of electrical insulators extending through the elongated member, each of the insulators having a lumen, wherein the elongated member has apertures extending along the exterior wall into each of the electrical insulators; a plurality of elongated electrode tines extending through the respective insulator lumens; and a plurality of side members associated with the proximal end of the elongated member, the side members mechanically connected to the respective electrode tines through the respective apertures for being operable to independently move the respective electrode tines to extend beyond, or retract within, the distal end of the elongated member.

There are some US patents teaching designs of cryosurgical probes or catheters with variable shapes of their distal tips. These include Yon (U.S. Pat. No. 7,001,378), Maguire (U.S. Pat. No. 6,954,977), Nohilly (U.S. Pat. No. 6,951,569), Lehmann (U.S. Pat. No. 6,942,659), Mihalik (U.S. Pat. No. 6,913,604), and Isoda (U.S. Pat. No. 6,995,493). Such patents can be divided into three categories:
1. Cryocatheters with inflatable cryotips.
2. Cryoprobes or cryocatheters with tubular spiral-wise cryotips.
3. Cryoprobes with linearly extending cryotips.

Vancelette (US Publication No. 20050177147) describes a cryoablation system which includes an elongated tubular cannula having a proximal end, a distal end, and a longitudinal axis, an expandable balloon extending from the distal end of the cannula and fluidly connected to a source of heat transfer fluid by at least one fluid path, a pump for circulating the heat transfer fluid into and out of the balloon, a probe handle coupled to the proximal end of the cannula and in fluidic communication with the balloon through the cannula, and a heat exchanger for varying the temperature of the heat transfer fluid, wherein the heat exchanger is fluidly connected to a secondary refrigerant source. The balloon is preferably expandable in response to an addition of a volume of heat transfer fluid. The heat exchanger may be positioned within the probe handle so that the secondary refrigerant can cool the heat transfer fluid to a treatment temperature before the heat transfer fluid is provided to the balloon, or the heat exchanger may alternatively be positioned within the console of the system so that the secondary refrigerant can cool the heat transfer fluid to a treatment temperature before the fluid is provided to the probe handle, or the heat exchanger may alternatively be positioned within the cannula so that the secondary refrigerant can cool the heat transfer fluid to a treatment temperature before the heat transfer fluid is provided to the balloon. In another alternative, the heat exchanger is positioned at least partially within the balloon.

SUMMARY OF THE INVENTION

The background art does not teach or suggest a cryoprobe or cryocatheter which allows an ice ball formed around the cryotip to be enlarged significantly, without inflating the cryotip and without substantial increase of the effective diameter of the cryotip itself. Also the background art does not teach or suggest a narrow cryogenic probe that can treat a relatively large volume of tissue.

The present invention overcomes these drawbacks of the background art by providing a narrow cryogenic probe that can treat a relatively large volume of tissue, optionally and preferably by permitting an ice ball having a diameter larger that of the cryotip to be formed around the cryotip, by permitting an increase of the effective diameter of the treatment area after the cryotip enters the tissue to be treated, through protrusion and displacement of at least one and preferably a plurality of needles.

BRIEF DESCRIPTION OF THE FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawings making apparent to those skilled in the art how the several forms of the invention may be embodied in practice.

In the accompanying drawings.

DESCRIPTION OF THE PREFERRED EMBODIMENTS

The present invention relates to novel cryogenic probes that are useful for a variety of medical applications, particularly surgical techniques such as cryoablation.

Such probes are useful for treating cysts and cancerous growths and, to be directed to a desired location, have to pass through healthy body tissue or through body cavities, and, to minimize trauma to healthy tissue, should be as narrow as possible. To effectively treat a cancerous growth, the volume of cryogenically frozen tissue should include all the cancerous cells. Thus it is desired that the effective diameter of the active part of the probe tip should be large. These are competing requirements.

The volume treatable by a single insertion of a single, acceptably narrow probe of the prior art may be insufficient to treat the full volume of tissue requiring treatment. The present invention provides a extendible probe tip, that is preferable configurable to extend sideways as necessary, between fully extended and fully retracted limits.

Figure 1:
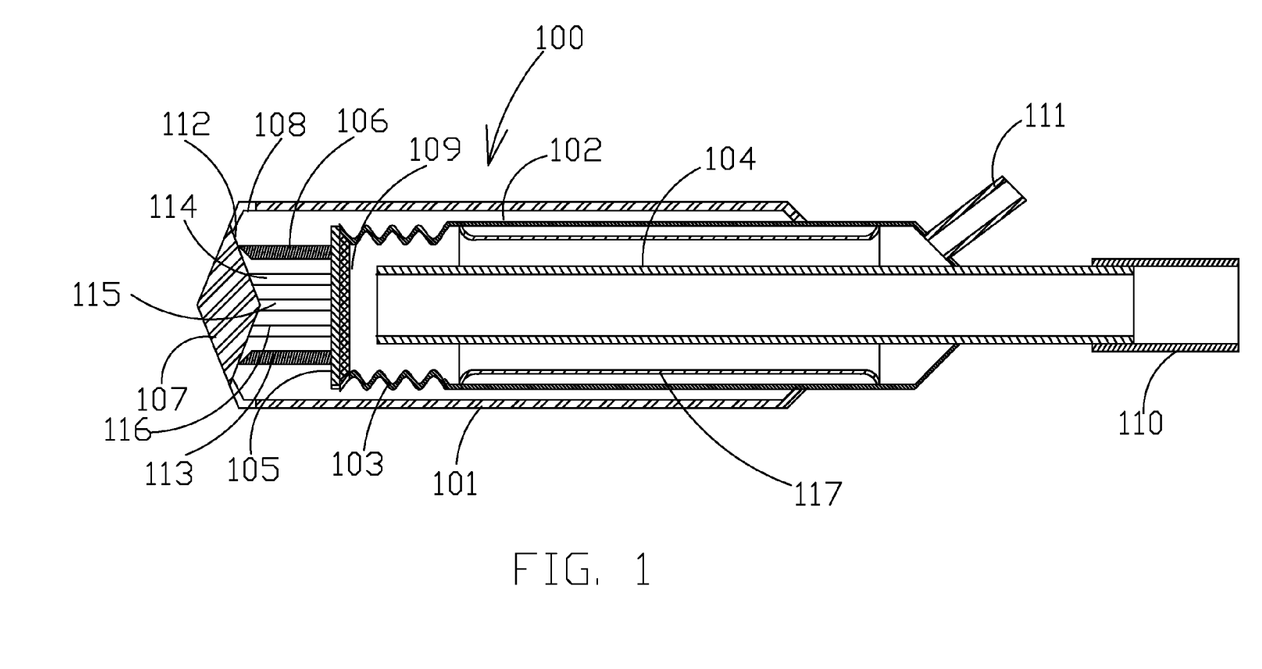
FIG. 1 is a schematic cross section through a cryogenic probe in accordance with a first embodiment of the present invention having solid needles, in its retracted position.

With reference to FIG. 1, a cryogenic probe 100 in accordance with a first embodiment of the present invention is shown. The cryogenic probe 100 is coupled to a cryogenic freezing system (not shown) via connector 110 that serves as an inlet for a cryogenic medium, optionally a cryogenic fluid. Connector 110 is preferably connected to an inner lumen 104 such that a cryogen entering through connector 110 is conveyed down inner lumen 104.

The cryogenic probe 100 preferably includes an intermediate lumen 102, such that inner lumen 104 is preferably located at least partially within intermediate lumen 102. Intermediate lumen 102 preferably terminates in an expandable element 103, which is optionally and more preferably in the form of bellows. Expandable element 103 is preferably sealed at the distal edge thereof by a face plane 105 to the outer side of which a needle array 106 is appended, such that needle array points forwards, parallel to axis of the intermediate lumen. Face plane 105 may optionally be any type of supporting element for needle array 106 (which may optionally comprise only one needle but which preferably comprises a plurality of needles) which preferably also closes or seals expandable element 103.

Figure 2:
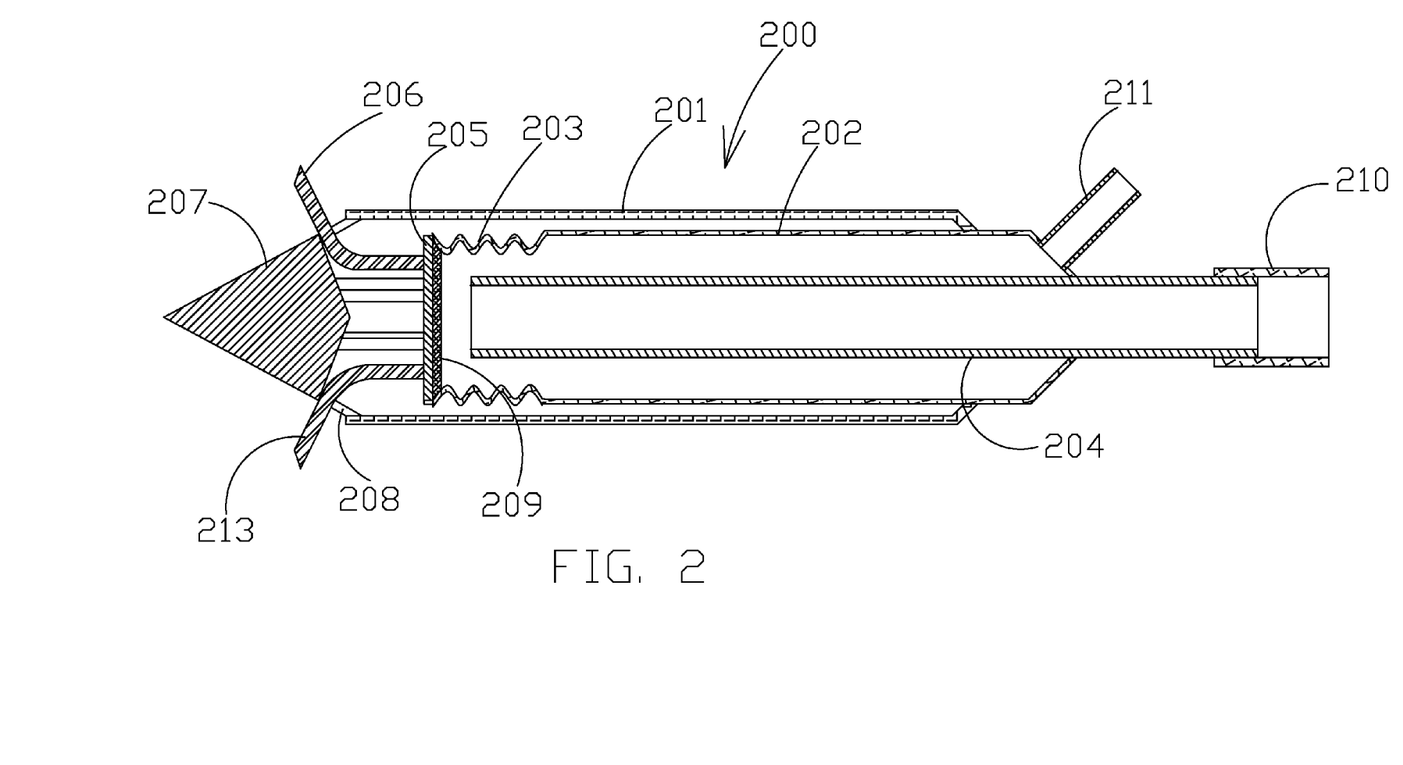
FIG. 2 is a schematic cross section through the cryogenic probe of FIG. 1 in its extended position with extended needles.

Due to the expanding or contracting action of expandable element 103, the needle array 106 may optionally and preferably be displaced both frontwards and backwards, thereby being extended and retracted via apertures 108 in the cryoprobe tip. The intermediate lumen 102 is preferably coupled to an external lumen 101 at a distal end thereof. The external lumen 101 preferably has a high rigidity and comprises thermal insulation means 117. By displacement of expandable element 103, the face plane 105 and the needle array 106 can preferably be displaced, for example between a retracted position shown in FIG. 1, and an extended position as shown in FIG. 2.

At the distal end of the external lumen 101, a blunt tip 107 is preferably provided, having a deflecting member 112 on an inner surface thereof. If expandable element 103 is expanded, a plurality of needles 113-116 (of which four are shown for the sake of illustration only and without any intention of being limiting) are displaced forwards and are deflected sideways and outwards by deflecting member 112. This results in the needle(s) 113-116 protruding outwards from the distal end of probe 100, and assuming the extended position shown in FIG. 2. In this manner the needle(s) 113-116 can provide a cryogenic freezing effect in body tissue situated a larger distance away from tip 107 and the external lumen 101. This increases the effective area treated by probe 100 without actually enlargement of the diameter of the probe 100.

Intermediate lumen 102 is preferably provided with an outlet connection 111, which serve for venting the gaseous phase of the cryogen after use, are also optionally and preferably provided. Preferably, inner lumen 104 is open at the distal end to permit the cryogenic material to cool the distal end of probe 100; gases are then preferably vented through intermediate lumen 102.

Probe 100 is designed for insertion into a portion of the body, and should, to minimise damage to tissue during its insertion and removal, be as narrow as possible. This is accomplished by having an actual diameter of the cryotip that is significantly smaller than the effective diameter upon splaying out of needles 113-116, such that once needles 113-116 are retracted, the cryotip is actually quite narrow, only requiring a narrow aperture in the body for insertion and removal.

The cryogen is preferably carried to the distal end of the inner lumen 104 to allow the cryogen to coolingly expand at distal end of the inner lumen 104 within expandable element 103. Such an expansion preferably both displaces face plane 105 forwards and providing a cryogenic freezing effect at the distal end of the probe 100, such that the expansion of the cryogen preferably occurs close to the needle array 106. If a cyrogenic liquid is used, it is able to boil on the inner surface of the face plane 105 that is optionally and preferably provided with a porous coating 109 with open capillary structure so that the cryogenic fluid is able to coolingly boil.

Optionally the flexible needles 113-116 are all identical, but need not be. In the embodiment of FIG. 1 and 2, the face plane 105 is displacing forwards and the proximal ends of needles 113-116 are cooled by thermal conductivity from face plane 105. Needles may optionally be made from silver, copper, brass and/or various other alloys as could easily be selected by one of ordinary skill in the art.

The blunt tip 107 of probe 100 is preferably fabricated from a metal having a high thermal conductivity coefficient, such as silver, for example. The deflecting member 112 on the inner surface thereof preferably has a shape suitable for smoothly deflecting the flexible needle(s) 113-116, such as a cone or spherical shape, for example. The inner surface of the face plane 105 may optionally be coated with a porous coating 109 having an open porosity to provide a large surface to encourage cryogenic fluid to boil thereon, providing the cryogenic freezing effect when a liquid cryogen is used.

FIG. 2 shows the axial section of the cryoprobe with the expandable cryotip in its operation state for treatment of tissue (where the internal pressure in the internal space of the cryoprobe is optionally and preferably higher than the atmospheric pressure). Unless otherwise noted, the numbered elements shown in FIG. 2 correspond to the numbered elements of FIG. 1 when the number of such an element in FIG. 2 is equal to that of the number in FIG. 1 plus 100.

In some embodiments, such as that shown in FIGS. 1 and 2, the flexible needle(s) 113-116 are solid and the proximal end(s) thereof are directly cryogenically cooled, with the distal end(s) thereof being cooled by thermal conduction therealong.

Figure 3:
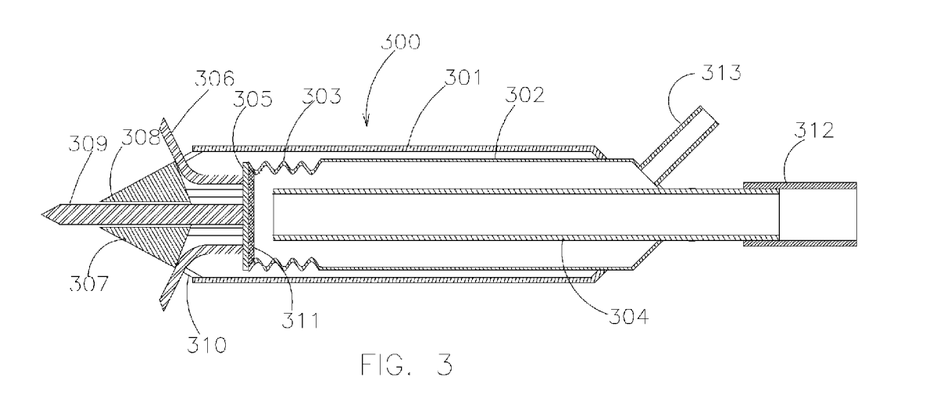
FIG. 3 is a schematic cross section through a cryogenic probe in accordance with a second embodiment of the present invention.

Referring now to FIG. 3, in a second embodiment, mutatis mutandis, the cryogenic probe 300 may additionally include an additional extending needle 309 for being extended through a central hole 308 in the deflecting member 307.

Internal surface of face plane 305 optionally and preferably features a porous coating 311 with open porosity for absorbing the cryogenic medium, thereby improving heat transfer to face plane 305. A connector 312 permits cryogenic medium to enter an inner lumen 304, as for connector 110 and inner lumen 104 of FIG. 1. An outlet connection 313 is provided, similar to outlet connection 111 of FIG. 1. An external lumen 301 is provided, similar to external lumen 101 of FIG. 1. An expandable element 303 is provided, similar to expandable element 103 of FIG. 1.

Central needle 309 preferably protrudes from this central opening 308 upon an increase of pressure in the internal space of the intervening lumen 302. In addition, the distal section of the external shaft is provided with openings 310 for allowing needles 306 to protrude.

Figure 4:
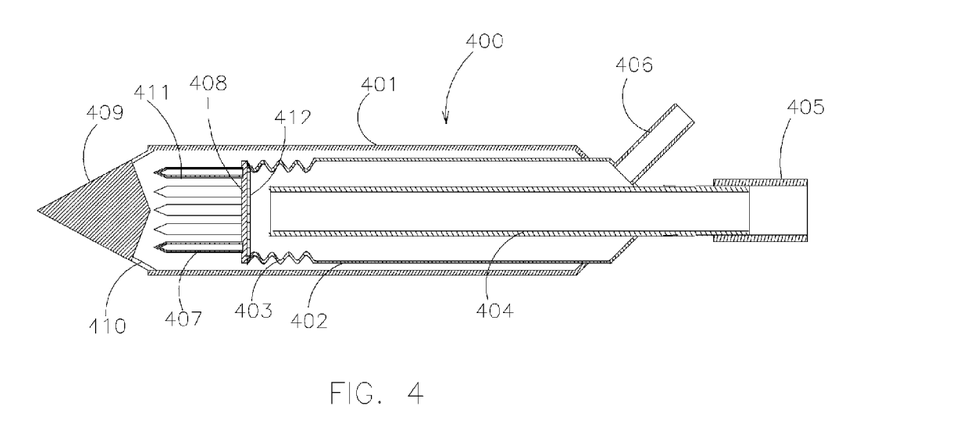
FIG. 4 is a schematic cross section through a cryogenic probe in accordance with a third embodiment of the present invention.

Referring to FIG. 4, in a third embodiment, mutatis mutandis, the flexible needle(s) 407 of probe 400 are preferably sealed hollow needle(s) having closed proximal end(s) and closed distal end(s), with the needles preferably serving as heat pipe(s), i.e. they are filled with a cryogen, such that movement of cryogen in the internal space of the needle allows effective heat transfer from the proximal section of each needle to its distal section. The inner walls of needles 407 are preferably provided with a porous coating 411 with open porosity. In case of a liquid cryogen, the cryogen may also comprise a gaseous phase or alternatively may only feature a gaseous phase after boiling of the liquid. A face plane 408 is also preferably provided with a porous coating 412 as previously described with regard to FIG. 3 (face plane 305 and porous coating 311). A connector 405 and an outlet connection 406 are provided as previously described with regard to FIGS. 1-3 (see for example connector 110 and outlet connection 111 of FIG. 1). A deflector 409 is provided as is a plurality of openings 410 in the distal section of the external shaft for allowing needles 407 to protrude.

Numbered elements 401-404 shown in FIG. 4 correspond to the numbered elements of FIG. 1 when the number of such an element in FIG. 4 is equal to that of the number in FIG. 1 plus 300.

Figure 5:
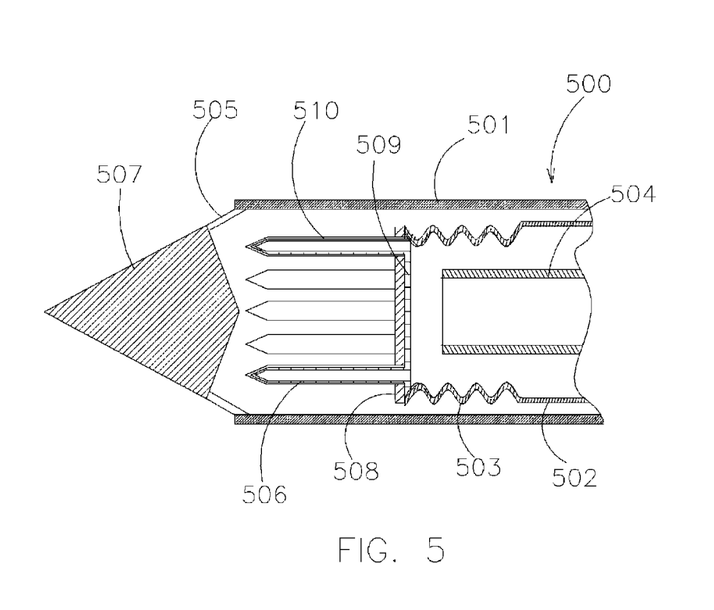
FIG. 5 is a schematic cross section through a cryogenic probe in in accordance with a fourth embodiment of the present invention having hollow needles.

As shown in FIG. 5, in a further embodiment, the enlarged axial section of the distal part of a cryoprobe 500 features needles optionally constructed as open heat pipes. Each needle 506 is preferably constructed as a heat pipe; the internal walls of each heat pipe are optionally and more preferably provided with a porous coating 510. The internal surface of the face plane 508 is coated by a porous metal coating 509 with open porosity. The internal spaces of needles 506 are preferably in fluid communication with the internal space of the intervening lumen 502, and the porous metal coatings 510 of needles 506 are in capillary communication with the porous coating 509 of the face plane 508, such that porous metal coatings 510 are preferably in physical contact with porous coating 509 to permit capillary action from one coating to the other coating. In such a way, the needles 506 are functioning as heat pipes, when the cryogen is delivered via the central feeding lumen 504 on the porous metal coating 509.

Again, the needles 506 are displaced by the deflecting member 507 when they are displaced forwards by expandable element 503.

The cryprobe 500 also features an external lumen 501 and an opening 505 (for permitting passage of the needles 506) as previously described.

In various embodiments, the cryogenic probe may optionally and preferably be coupled to a cryogenic cooling system that uses a liquid cryogen such as liquid nitrous oxide, liquid argon or liquid nitrogen, or a gaseous cryogen, such as pressurized gaseous argon or nitrous oxide, for example, or dispersion such as a mist for example (liquid droplets dispersed in gaseous medium ), or a combination of two or more liquid cryogens or two or more gaseous cryogens.

In various embodiments, the cryogenic probe may optionally be coupled to a cryogenic cooling system that uses a liquid cryogen such as liquid nitrous oxide, liquid argon or liquid nitrogen, or a highly pressurized gaseous cryogen which should be expended via an orifice installed on the distal end of the central feeding lumen with its partial liquefying. In the last case, the distal section of the cryoprobe is provided with a counter-flow heat exchanger (a common design of a cryoprobe, which operates on the basis of the Joule-Thomson effect).

Figure 6:
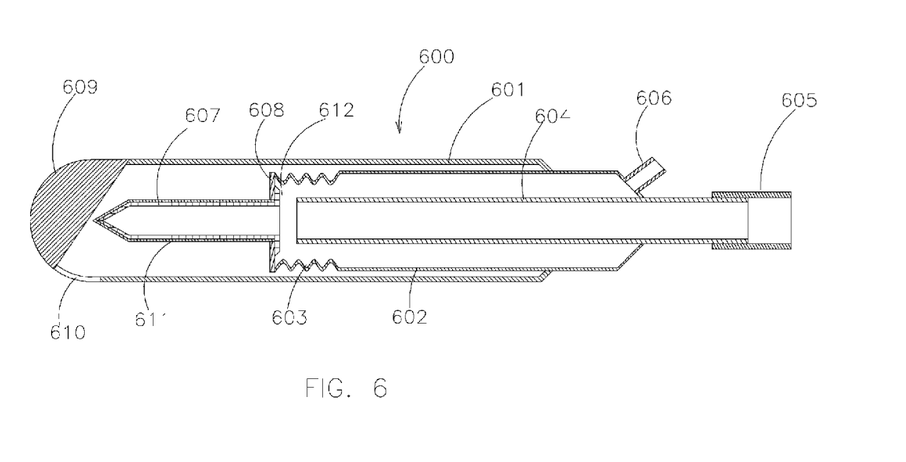
FIG. 6 is a schematic cross section through a cryogenic probe having a single needle probe that extends sideways out of the cylinder when it is displaced forwards by the a unidirectional expandable element thereof.

As shown in FIG. 6, in an optional variation, probe 600 has only one needle 607 provided at the distal end of a face plane 608. The face plane 608 is preferably joined sealingly with expandable element 603 and a deflecting member 609 is shaped to deflect needle 607 through an apperture 610 to protrude outward from shaft 601 of probe 600.

Needle 607 is optionally constructed as an open capillary heat pipe; the internal wall of this capillary heat pipe is provided with a porous coating 611.

The internal surface of the face plane 608 is optionally and preferably coated with a porous metal coating 612 with open porosity.

The internal space of the central needle 607 is in fluid communication with the internal space of the intervening lumen 602, and the porous metal coating 612 of the central needle 607 is in capillary communication with the porous coating 611 of the face plane 607.

In this manner, the needle-wise element 607 functions as an open heat pipe, when the cryogen is delivered via the central feeding lumen 604 on the porous metal coating 611.

As previously described, the probe 600 features a connector 605 (corresponding to connector 110 of FIG. 1) and an outlet 606 (corresponding to outlet 111 of FIG. 1).

The cryogenic probes of the present invention may optionally and preferably be used in a wide range of surgical applications including, inter alia, to treat cancerous growths, for treating breast cancer, for liver surgery, gynecology, and brainsurgery.

Figure 7A:
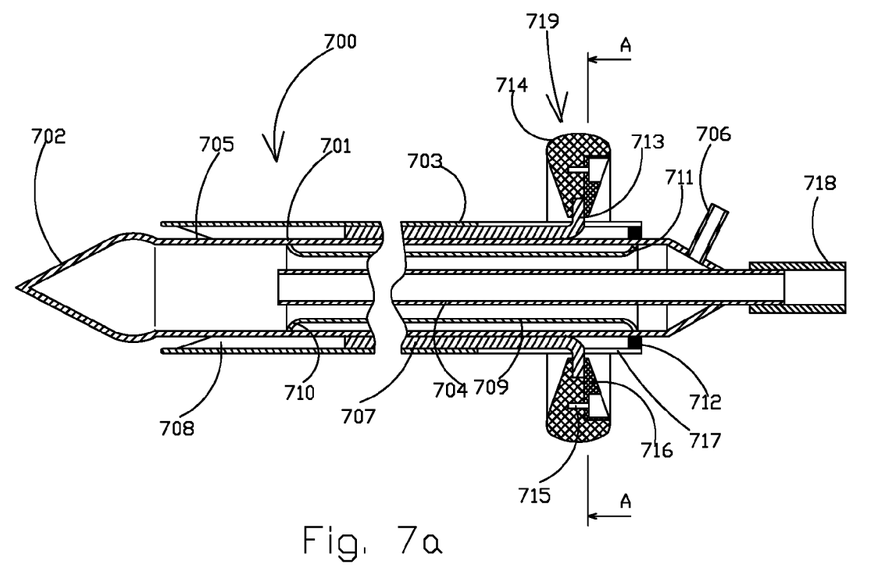
FIGS. 7A and 7B are schematic axial cross-sections of a cryogenic probe having a displaceable metal sheath with a split or bifurcated distal end and a stationary external sheath, in which the displaceable sheath may be located in one of two extreme positions.
Figure 7B:
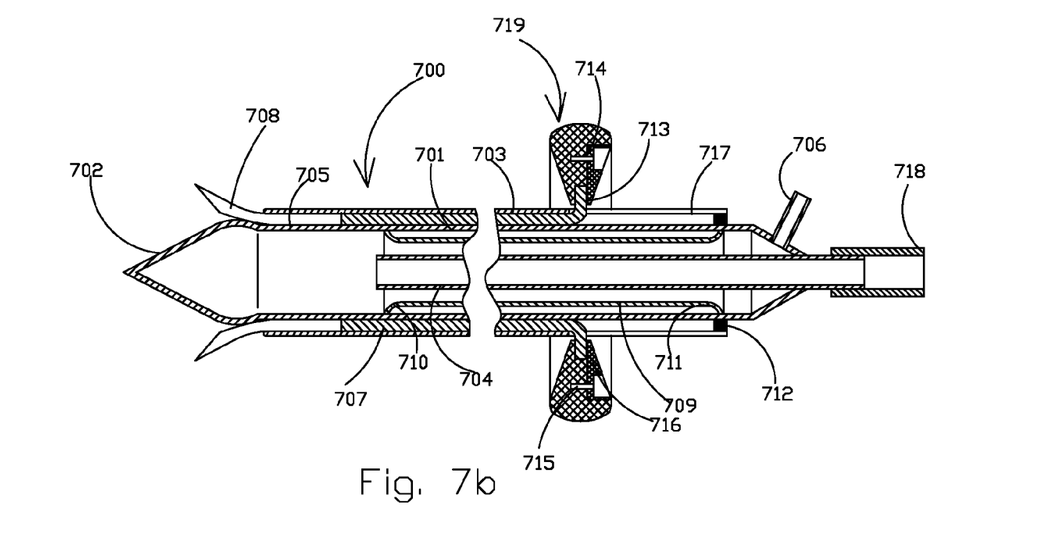
Figure 7C:
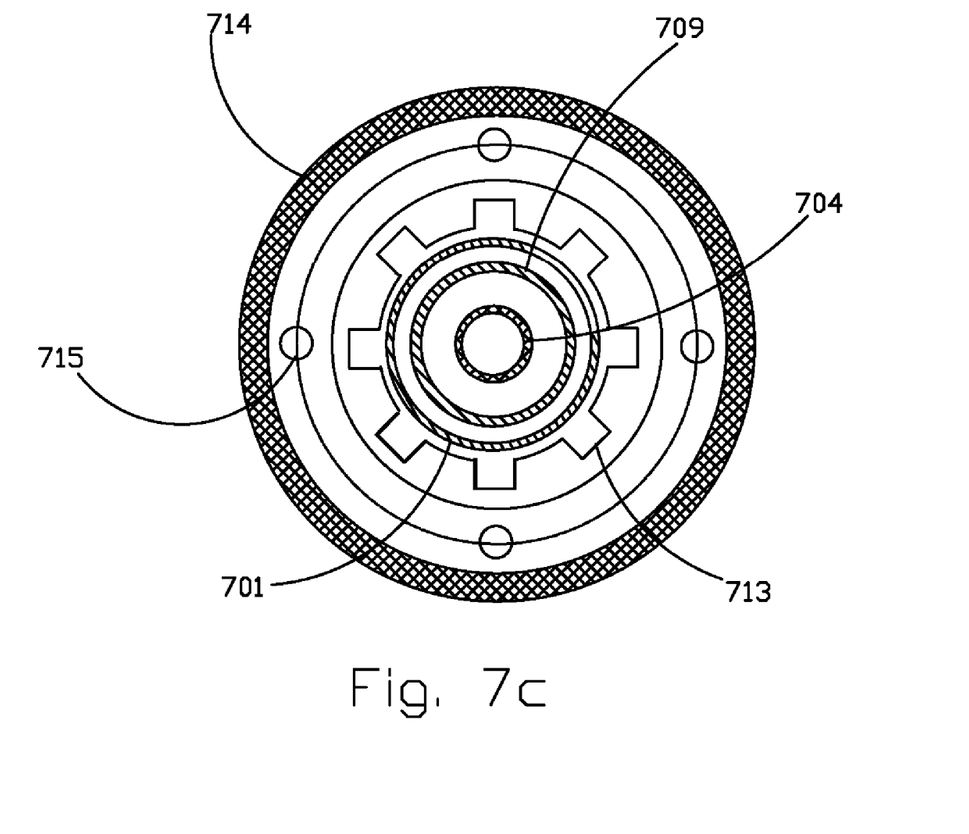
FIG. 7C is a radial cross-section of a cryogenic probe in the plane of the proximal elbow bends of the metal displaceable sheath.

FIGS. 7A and 7B are schematic axial cross-sections of a cryogenic probe having a displaceable sheath with an end split into a plurality of sections, each of which is preferably pointed (narrowed) and a stationary external sheath, in which the displaceable sheath may be located in one of a plurality of positions. The displaceable sheath may, in its distal section, optionally and preferably be fabricated from metal with high thermal conductivity. FIG. 7C shows a radial cross-section of a cryogenic probe in the plane of the proximal elbow bends of the metal displaceable sheath.

The cryoprobe 700 comprises an external shaft 701 with a distal end 702, which is preferably bulbous, and a distal freezing section 705. By "bulbous" it is meant that distal end 702 is distended or widened for at least one portion and is narrowed for at least a second portion, such that the width of the first portion is greater than the width of the second portion; the widened portion is preferably but not necessarily rounded.

There is a central feeding lumen 704 with a proximal inlet connection 718 for supplying a cryogenic medium into the distal section of 705 of the cryoprobe 700 and for cooling distal freezing section 705 to a cryogenic temperature. The proximal edge of the external shaft 701 is sealed with the central feeding lumen 704 and the proximal section of the external shaft is provided with an outlet connection 706 for exhausting cryogenic gas.

A thermal insulating tube 709 for insulating the cryogenic medium in the central feeding lumen 704 is preferably situated between the central feeding lumen 704 and the external shaft 701 and fastened by outward flangings 710 and 711 to the external shaft 701.

A displaceable (and preferably metal) sheath 707 is positioned on the external shaft 701; this displaceable metal sheath 707 is preferably provided with a split distal section forming a plurality of sections which are preferably needles 708 as shown. In addition, the proximal section of the displaceable sheath 707 is preferably provided with a plurality of notches (not shown). The displaceable sheath 707 preferably features a plurality of elbow bends 713. These elbow bends 713 fasten handle 719 assembled from two annular members 714 and 716. Annular members 714 and 716 are preferably provided with openings 715 for joining these annular members 714 and 716 by screws (not shown).

A stationary external sheath 703 preferably at least partially surrounds the displaceable sheath 707 and is preferably joined to the external shaft 701 by a joining ring 712. The proximal section of the stationary external sheath 703 is preferably provided with notches 717 allowing controlled displacement of the displaceable sheath 707 with regard to external sheath 703, due to displacement of a plurality of the elbow bends 713 on displaceable sheath 707.

Displaceable sheath 707 is preferably located in a proximal location for entry to the tissue (see FIG. 7A). Displaceable sheath 707 is preferably located in a distal location during cryogenic treatment (see FIG. 7B). During such treatment, distal end 702 is preferably placed in, at or near the tissue to be treated, and cryogenic medium flows through proximal inlet connection 718 to cool distal freezing section 705 to a cryogenic temperature. This reduction in temperature may cause a cryogenic iceball to form at distal end 702.

For displacement to occur, the displaceable sheath 707 is moved forward by pushing on the handle 719 assembled from the annular members 714 and 716. Upon displacement of the displaceable sheath 707, needles 708 are displaced forward as well. The distended (and preferably curved) surface of distal end 702 preferably causes needles 708 to protrude outward, away from the distal freezing section 705. These needles 708 facilitate heat transfer from the distal freezing section 705 into the tissue surrounding this distal freezing section 705 (not shown), thereby lowering the temperature of the formed ice ball while the cryogenic medium is being provided, as the effective diameter of the cryotip is enlarged. As appropriate, for example after sufficient cryotreatment, the cryogenic medium is no longer supplied and the ice ball thaws. After thawing the formed ice ball, needles 708 are displaced back by backward displacement of the handle 719 assembled from the annular members 714 and 716 (to the position of FIG. 7A).

Figure 8A:
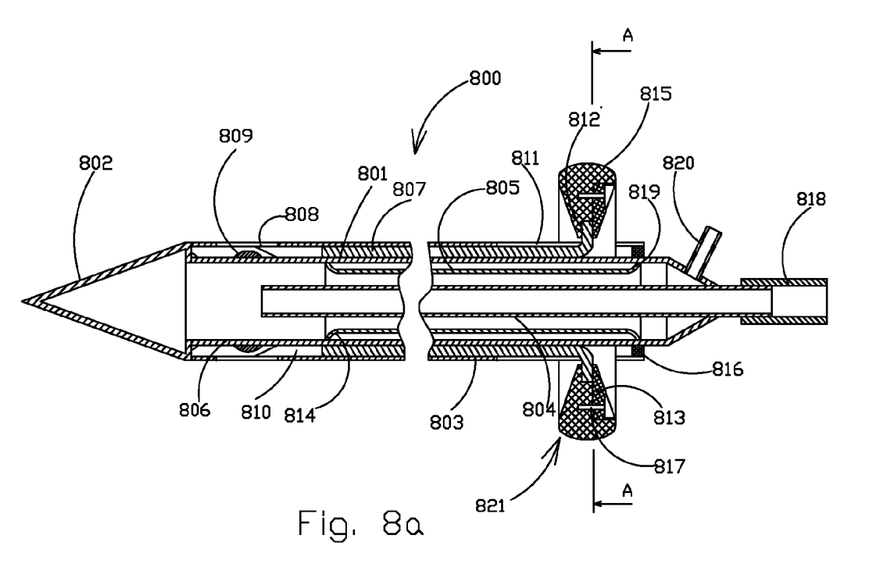
FIGS. 8A and 8B are schematic axial cross-sections of a cryogenic probe having a displaceable metal sheath with needles formed as cut-outs and a stationary external sheath, in which the metal displaceable sheath may be located in one of two extreme positions.
Figure 8B:
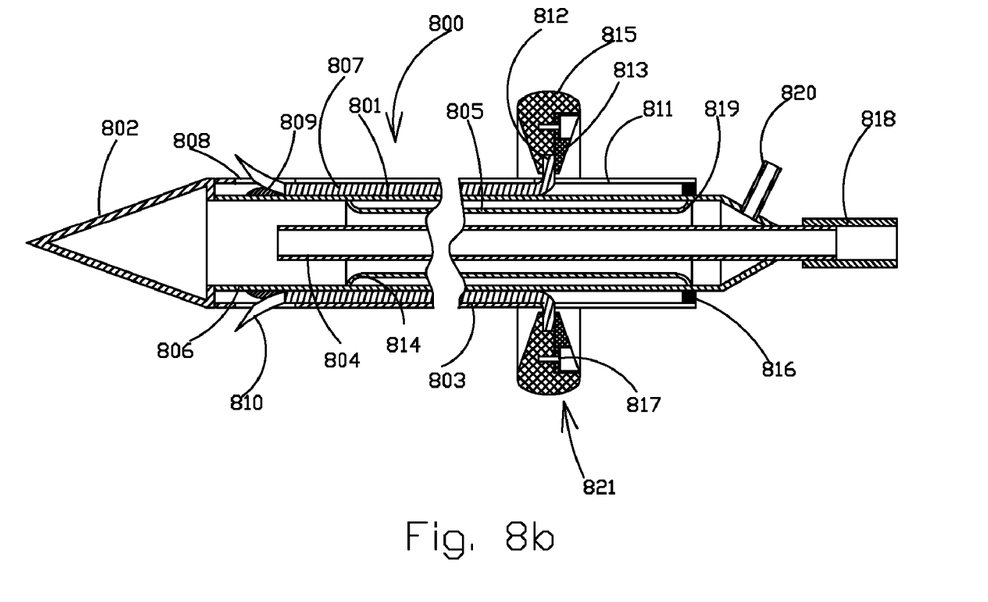
Figure 8C:
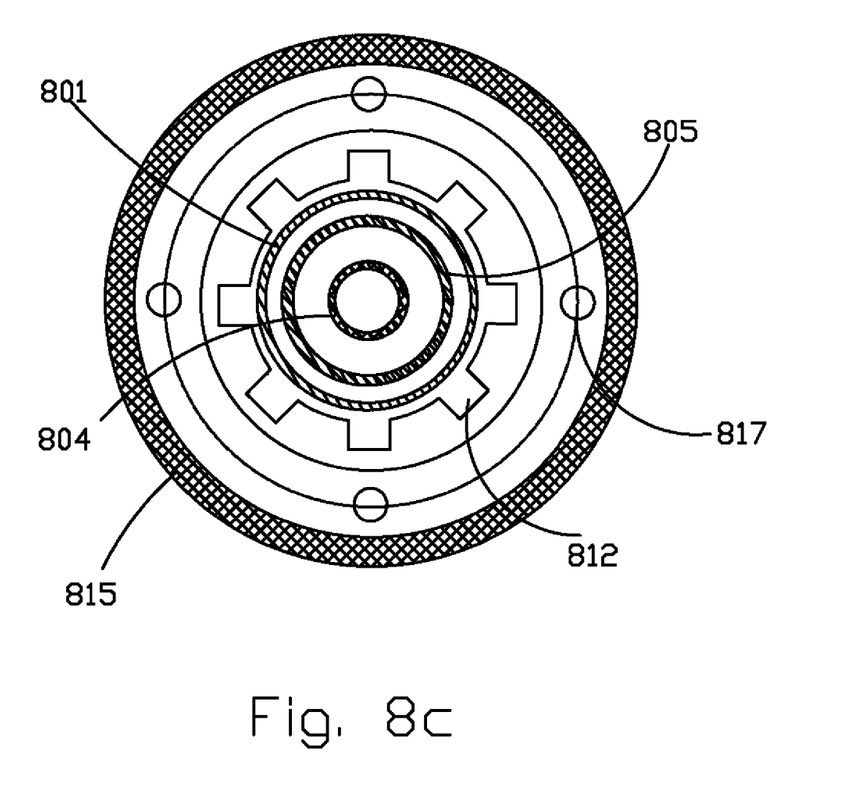
FIG. 8C is a radial cross-section of a cryogenic probe in the plane of the proximal elbow bends of the metal displaceable sheath.

FIGS. 8A and 8B are schematic axial cross-sections of a cryogenic probe having a displaceable sheath with needles formed as cut outs and a stationary external sheath, in which the displaceable sheath may be located in one of a plurality of positions. As for FIGS. 7A-C, the displaceable sheath preferably comprises metal. FIG. 8C shows a radial cross-section of a cryogenic probe in the plane of the proximal elbow bends of the displaceable sheath.

The cryoprobe 800 comprises an external shaft 801 with a distal end 802 and distal freezing section 806. Distal end 802 is optionally not bulbous and may optionally for example be narrowed at the tip as shown.

A central feeding lumen 804 features a proximal inlet connection 818 for receiving cryogenic medium. The proximal edge of the external shaft 801 is sealed with the central feeding lumen 804 and the proximal section of the external shaft 801 is provided with an outlet connection 820 for exhaust of gas obtained from the cryogenic medium. In addition, the distal outer section of the external shaft 801 is preferably provided with a plurality of protrusions 809.

A thermal insulating tube 805 is preferably situated between the central feeding lumen 804 and the external shaft 801 for insulating the cryogenic material in the central feeding lumen 804; thermal insulating tube 805 is preferably fastened by outward flangings 814 and 819 to the external shaft 801. A displaceable sheath 807 is positioned on the external shaft 801; this displaceable sheath 807 is provided with a split distal section forming a plurality of needles 810, preferably formed as cut-outs. In addition, the proximal section of the displaceable sheath is preferably provided with a plurality of notches and a plurality of elbow bends 812. These elbow bends 812 serve for fastening a handle 821 assembled from two annular members 815 and 813, which are preferably provided with openings 817 for being joined by screws (not shown).

A stationary external sheath 803 preferably at least partially surrounds the displaceable sheath 807 and is preferably joined with the external shaft 801 by a joining ring 816. The proximal section of the stationary external sheath 803 is preferably provided with a plurality of notches 811 allowing displacement of the displaceable sheath 807. In addition, the distal section of the stationary external sheath 803 is preferably provided with a plurality of longitudinal slots 808 to permit protrusion of needles 810 outwards.

The cryoprobe 800 preferably operates in a similar manner as shown in FIGS. 7A-7C for cryogenic treatment of tissue. The cryoprobe 800 is shown in cryogenic treatment form in FIG. 8B and for entry to the tissue in FIG. 8A. For treatment, as in FIG. 8B, the displaceable sheath 807 is preferably displaced, again by pushing on the handle 821 as for FIGS. 7A-7C. Now needles 810 are displaced forward, causing them to protrude outward from the distal freezing section 806, due to protrusions 809.

As for FIGS. 7A-7C, needles 810 facilitate heat transfer from the distal freezing section 806 into the tissue surrounding this distal freezing section 806. After thawing a formed ice ball, needles 810 are preferably displaced back by backward displacement of the handle 821 assembled from the annular members 815 and 813 (to the position of FIG. 8A).

While the invention has been described with respect to a limited number of embodiments, it will be appreciated that many variations, modifications and other applications of the invention may be made and still be within the spirit and scope of the invention.

Persons skilled in the art will appreciate that the present invention is not limited to what has been particularly shown and described hereinabove. Rather the scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

We claim:

1. A cryogenic probe comprising:
   a main lumen for receiving a cryogen;
   a face plane sealing a distal end of said main lumen, said face plane being reversibly displaceable in an axial direction;
   an expandable element incorporated into said main lumen, wherein said expandable element expands at least in the axial direction, and said expandable element comprises bellows for expanding upon elevation of operation pressure of cryogen in said main lumen;
   at least one needle fastened at its proximal end on an external side of said face plane; and
   a deflecting means, which causes deflection of said at least one needle sideways with displacement of said face plane.

2. The probe of claim 1, wherein said at least one needle comprises a thermally conductive flexible needle.

3. The probe of claim 1, further comprising a central lumen situated in said main lumen and delivering cryogen into said main lumen.

4. The probe of claim 1, wherein said deflecting means comprises an external lumen surrounding said main lumen and a deflecting member installed on a distal end of said external lumen for deflecting said at least one needle.

5. The probe of claim 4, wherein said external lumen comprises rigid, thermal insulating material.

6. The probe of claim 4, wherein the deflecting member comprises thermally conductive material.

7. The probe of claim 6, wherein an inner surface of the deflecting member has a shape suitable for smoothly deflecting at least one flexible needle.

8. The probe of claim 1, wherein said at least one needle comprises an array of a plurality of flexible needles, located on the external side of said face plane.

9. The probe of claim 8, wherein the plurality of the flexible needles comprises identical needles.

10. The probe of claim 8, wherein the flexible needles comprise solid, thermally conductive needles having cryogenically cooled proximal ends.

11. The probe of claim 8, wherein at least one flexible needle of said plurality of flexible needles comprises a hollow needle having an open proximal end, an internal capillary structure and a closed distal end.

12. The probe of claim 11, wherein said capillary structure comprises a porous coating with open porosity.

13. The probe of claim 11, wherein said capillary structure comprises a plurality of fibers.

14. The probe of claim 8, wherein said at least one flexible needle of said plurality of flexible needles comprises a hollow needle having a closed proximal end and a closed distal end.

15. The probe of claim 1, further comprising a cryogenic cooling system using a liquid cryogen.

16. A cryogenic probe comprising:
    a main lumen for receiving a cryogen;
    a face plane sealing a distal end of said main lumen, said face plane being reversibly displaceable in an axial direction;
    an array of a plurality of flexible needles located on an external side of said face plane, wherein said array of said flexible needles comprises at least one central needle displaced forwards with said face plane; and
    a deflecting means, which causes deflection of at least one needle of said plurality of flexible needles sideways with displacement of said face plane, and wherein said deflecting means includes an aperture for passage of said at least one central needle.

17. A cryogenic probe comprising:
    a main lumen for receiving a cryogen;
    a face plane sealing a distal end of said main lumen, said face plane being reversibly displaceable in an axial direction, wherein the face plane further comprises an internal porous coating having open pore porosity and providing a surface for boiling cryogen thereupon;
    at least one needle fastened at its proximal end on an external side of said face plane; and
    a deflecting means, which causes deflection of said at least one needle sideways with displacement of said face plane.

18. A cryogenic probe comprising:
    a main lumen for receiving a cryogen, wherein said main lumen comprises a conduit provided with a counter-flow heat exchanging means and a distal expansion orifice for receiving and allowing a high pressure gas to expand into said main lumen and to partially liquefy within said main lumen;
    a face plan sealing a distal end of said main lumen, said face plane being reversibly displaceable in an axial direction;
    at least one needle fastened at its proximal end on an external side of said face plane; and
    a deflecting means, which causes deflection of said at least one needle sideways with displacement of said face plane.

* * * * *